US011241302B2

(12) United States Patent
Cullison

(10) Patent No.: US 11,241,302 B2
(45) Date of Patent: Feb. 8, 2022

(54) SURGICAL METHOD

(71) Applicant: James W Cullison, Carrollton, GA (US)

(72) Inventor: James W Cullison, Carrollton, GA (US)

(*) Notice: Subject to any disclaimer, the term of this patent is extended or adjusted under 35 U.S.C. 154(b) by 80 days.

(21) Appl. No.: 16/577,984

(22) Filed: Sep. 20, 2019

(65) Prior Publication Data

US 2020/0008919 A1    Jan. 9, 2020

Related U.S. Application Data

(62) Division of application No. 15/181,003, filed on Jun. 13, 2016, now Pat. No. 10,463,466, which is a division of application No. 14/429,684, filed as application No. PCT/US2014/032553 on Apr. 1, 2014, now Pat. No. 9,398,942.

(60) Provisional application No. 61/819,097, filed on May 3, 2013.

(51) Int. Cl.
*A61F 2/00* (2006.01)

(52) U.S. Cl.
CPC ............ *A61F 2/0036* (2013.01); *A61F 2/004* (2013.01); *A61F 2/0004* (2013.01); *A61F 2/0045* (2013.01); *A61F 2/0063* (2013.01); *A61F 2250/0003* (2013.01)

(58) Field of Classification Search
CPC .... A61F 2/0036; A61F 2/0004; A61F 2/0063; A61F 2/004; A61F 2/0045; A61F 2250/0003
See application file for complete search history.

(56) References Cited

U.S. PATENT DOCUMENTS

| | | | |
|---|---|---|---|
| 4,969,474 A | | 11/1990 | Schwarz |
| 5,123,428 A | * | 6/1992 | Schwarz ............... A61F 2/0036 |
| | | | 128/885 |
| 6,042,534 A | | 3/2000 | Gellman |
| 6,960,160 B2 | | 11/2005 | Browning |
| 7,104,949 B2 | | 9/2006 | Anderson et al. |
| 7,163,506 B2 | | 1/2007 | Grise |
| 7,204,801 B2 | | 4/2007 | Grocela |
| 7,878,969 B2 | | 2/2011 | Chu et al. |
| 7,975,698 B2 | | 7/2011 | Browning |
| 8,195,296 B2 | | 6/2012 | Longhini et al. |

(Continued)

FOREIGN PATENT DOCUMENTS

| | | |
|---|---|---|
| AT | 10932 U1 | 1/2010 |
| ES | 2226546 | 3/2005 |

(Continued)

OTHER PUBLICATIONS

Neumann, Elisabeth "Extended European Search Report—EP App No. 20187806.3" Sep. 29, 2020.

(Continued)

*Primary Examiner* — Kaylee R Wilson
(74) *Attorney, Agent, or Firm* — Nicholas J. Landau; Bradley Arant Boult Cummings LLP

(57) ABSTRACT

A method is provided for maintaining the position of pelvic organs, such as components of the urinary tract. The method may involve anchoring the pelvic organs by inserting the implant via an anterior approach, avoiding complications and side effects that result when implants are inserted through the wall of the vagina.

24 Claims, 10 Drawing Sheets

(56) References Cited

U.S. PATENT DOCUMENTS

| | | |
|---|---|---|
| 8,211,004 B1 | 7/2012 | Wijay et al. |
| 2001/0018549 A1 | 8/2001 | Scetbon |
| 2003/0114866 A1 | 6/2003 | Ulmsten et al. |
| 2004/0039453 A1 | 2/2004 | Anderson |
| 2004/0143152 A1 | 7/2004 | Grocela |
| 2004/0215054 A1 | 10/2004 | Siegel et al. |
| 2005/0055104 A1 | 3/2005 | Arnal et al. |
| 2005/0080317 A1 | 4/2005 | Merade |
| 2005/0101834 A1 | 5/2005 | Merade |
| 2006/0122457 A1 | 6/2006 | Kovac et al. |
| 2006/0134159 A1 | 6/2006 | Nicita |
| 2006/0229493 A1 | 10/2006 | Weiser |
| 2006/0264698 A1 | 11/2006 | Kondonis et al. |
| 2007/0049790 A1 | 3/2007 | Wagner |
| 2008/0269547 A1 | 10/2008 | Hortenstine |
| 2008/0269548 A1 | 10/2008 | Vecchiotti et al. |
| 2009/0062600 A1 | 3/2009 | Hallum |
| 2009/0112052 A1 | 4/2009 | Lund et al. |
| 2009/0171143 A1 | 7/2009 | Chu et al. |
| 2009/0227832 A1 | 9/2009 | Bauer |
| 2010/0030016 A1 | 2/2010 | Knoll |
| 2010/0168505 A1 | 7/2010 | Inman et al. |
| 2010/0174134 A1 | 7/2010 | Anderson et al. |
| 2011/0207992 A1 | 8/2011 | Morey |
| 2011/0245590 A1 | 10/2011 | Jacquetin |
| 2012/0215060 A1 | 8/2012 | Rosenblatt |
| 2012/0253109 A1 | 10/2012 | Vandeweghe et al. |
| 2013/0110137 A1 | 5/2013 | Nicolo |

FOREIGN PATENT DOCUMENTS

| | | |
|---|---|---|
| WO | 9831301 | 7/1998 |
| WO | 2002098322 | 12/2002 |
| WO | 2006084167 | 8/2006 |
| WO | 2013020076 | 2/2013 |

OTHER PUBLICATIONS

Botros, Sylvia, et al. "Following midurethral versus bladder sling procedures" American Journal of Obstetrics and Gynecology (2005) 193 Jul. 5, 2005.

Copenheaver, Blaine R. "International Search Report and Written Opinion—International Application No. PCT/US2014/032553"—United States—International Searching Authority; Dec. 9, 2014; pp. 1-15.

Hubka, et al. "Variation of Distances From Mid-Uretha to the Obturator Foramen: An MRI Study" Int Urogynecol J. 23(8); 1075-1080; Aug. 23, 2012.

Ridgeway, et al. "Variation of the obturator foramen and pubic arch of the femal bony pelvis" American Journal of Obstetrics & Gynecology; 198:546 May 1, 2008.

FDA CDRH "Urogynecologic Surgical Mesh: Update on the Safety and Effectiveness of Transvaginal Placement for Pelvic Organ Prolapse" Jul. 1, 2011.

Neumann, Elisabeth "Supplementary European Search Report—European patent application No. EP14791381.6" Mar. 2017; pp. 1-8.

\* cited by examiner

SURGICAL METHOD

CROSS-REFERENCE TO RELATED APPLICATIONS

This is a division of U.S. patent application Ser. No. 15/181,003, filed 13 Jun. 2016 (pending). U.S. patent application Ser. No. 15/181,003 is a divisional application of Ser. No. 14/429,684, filed 9 Mar. 2015, which is now U.S. Pat. No. 9,398,942. U.S. patent application Ser. No. 14/429,684 is a national stage of Int. Pat. App. No. PCT/US14/32553, filed 1 Apr. 2014, which is abandoned. Int. Pat. App. No. PCT/US14/32553 cites the priority of U.S. Pat. App. No. 61/819,097, filed 3 May 2013, which is expired. The disclosures of both of U.S. patent application Ser. No. 14/429,684 and Int. Pat. App. No. PCT/US14/32553 are incorporated herein in their entireties; the prosecution histories of these applications are not incorporated by reference.

BACKGROUND

A. Field of the Disclosure

The present disclosure relates generally to the treatment of urological disorders. Methods of treating such disorders, implants for the treatment of such disorders, and methods of using said implants, are provided.

B. Background

The muscles and ligaments that form the pelvic floor serve two critical functions in female physiology: controlling the flow of urine from the bladder and maintaining the positions of pelvic organs. When the floor weakens, is injured, stretches, or atrophies, the result can be urinary incontinence (UI) and pelvic organ prolapse (POP). POP is the descending or drooping of pelvic organs, such as the bladder, uterus, vagina, small bowel, and rectum. When it occurs, POP can result in the movement of one or more pelvic organs into another organ, for example prolapse of the bladder into the vagina. Other pelvic floor disorders include vaginal prolapse, vaginal hernia, rectocele, enterocele, uterocele, and urethrocele. POP and urinary incontinence are relatively common (about 30% of women in the United States experience some degree of pelvic organ prolapse in their lifetimes, and about 12% of U.S. women aged 60-64 experience urinary incontinence on a daily basis).

Pelvic floor disorders often cause or exacerbate female urinary incontinence. One type of urinary incontinence, called stress urinary incontinence, effects primarily women and is often caused by two conditions: intrinsic sphincter deficiency (ISD) and hypermobility. These conditions may occur independently or in combination. In ISD, the urinary sphincter valve, located within the urethra, fails to close properly, causing urine to leak out of the urethra during stressful activity. In hypermobility, the pelvic floor is distended, weakened, or damaged. When the afflicted woman sneezes, coughs, or otherwise strains the pelvic region, the bladder neck and proximal urethra rotate and descend. As a result, the urethra does not close with sufficient response time, and urine leaks through the urethra.

Various techniques have been used to anchor the pelvic organs to treat prolapse and to compress or support the urethra to prevent urinary incontinence. However, the performance of these traditional surgical techniques for these purposes has been poor.

Traditionally, both of these problems were fixed by repairing the patient's own tissue defects or by placing a non-synthetic implant underneath the urethra through an abdominal incision alone or in combination with a transvaginal incision. However, these approaches had unacceptable failure rates, long surgical times, long hospital stays, and significant postoperative pain. They were also criticized for requiring the patient's own tissues for support (specifically, the periurethral and perivesical fascia), which had the disadvantages of requiring that implants be custom fitted to the specific patient's dimensions and requiring that the patient had tissues of adequate strength. In addition, this approach used grafted tissue to form the implant, which in some cases would degrade with time.

In the late 1990s a new procedure was introduced for treating incontinence involving the insertion of a sling around the urethra made of synthetic mesh. The "midurethral sling" gained instant popularity over traditional transabdominal approaches and graft suburethral slings. It was simple to insert; the suburethral mesh sling could be introduced through a small transvaginal incision during an outpatient procedure in less than an hour. It required only a short recovery time with less postoperative pain. The synthetic mesh maintained its integrity over time and proved to be more durable than the patient's own tissue or cadaver tissue. The previously described techniques declined in number or were abandoned.

Unfortunately the new approach proved to have serious long-term side effects. The placement of the mesh posterior to the urethra creates a situation in which the mesh can press into the vagina, causing symptoms such as dyspareunia (painful intercourse), pelvic pain, anterior vaginal thinning, and erosion of the mesh into the vagina. These side effects can only be resolved by another procedure to remove the mesh. As a result, the patient often suffers worse symptoms than she did before the first procedure.

Consequently there is a need for a transabdominal approach to using non-absorbable material to treat POP and UI without the serious risks associated with the transvaginal approach.

SUMMARY

This application provides methods and devices to address the needs in the art discussed above; although it is to be understood that not every embodiment of such methods and devices will address any or all such problems.

A surgical implant for maintaining the position of a patient's urethra is provided. A general embodiment of the implant comprises: a proximal portion having a width, length, and thickness, the width of the proximal portion being at least 4× its length and at least 100× its thickness, the proximal portion comprising a first non-absorbable biocompatible material; and a distal portion having a width, length, and thickness, the width of the distal portion being no more than 0.25× the width of the proximal portion, and the thickness of the distal portion being no more than 0.01× the width of the proximal portion, the distal portion comprising a second non-absorbable biocompatible material.

Another general embodiment of the implant comprises: a proximal portion having a first width, a first length, and a first thickness, comprising a first non-absorbable biocompatible material; and a distal portion having a second width, a second length, and a second thickness comprising a second non-absorbable biocompatible material; wherein the ratio of the first width to the second width is at least the ratio of the distance between a given human's right and left pectineal ligament to the distance between the given human's right and left periurethral fascia.

A method of emplacing a surgical implant against the anterior urethra of a subject is also provided, the method comprising: anchoring the proximal portion of an implant to the right pelvic fascia of the subject and to the left pelvic fascia of the subject so that the implant is positioned between the bladder and the pubic bone and in contact with the anterior surface of the bladder; and anchoring the distal portion of the implant to the periurethral fascia of the subject; so that the distal portion of the implant contacts the anterior surface of at least one structure selected from: the bladder neck and the proximal urethra.

A method of supporting the proximal urethra or bladder neck of a subject is also provided, comprising fixating at least one of the proximal urethra and the bladder neck, from the anterior side.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

A. Definitions

Figure 1:
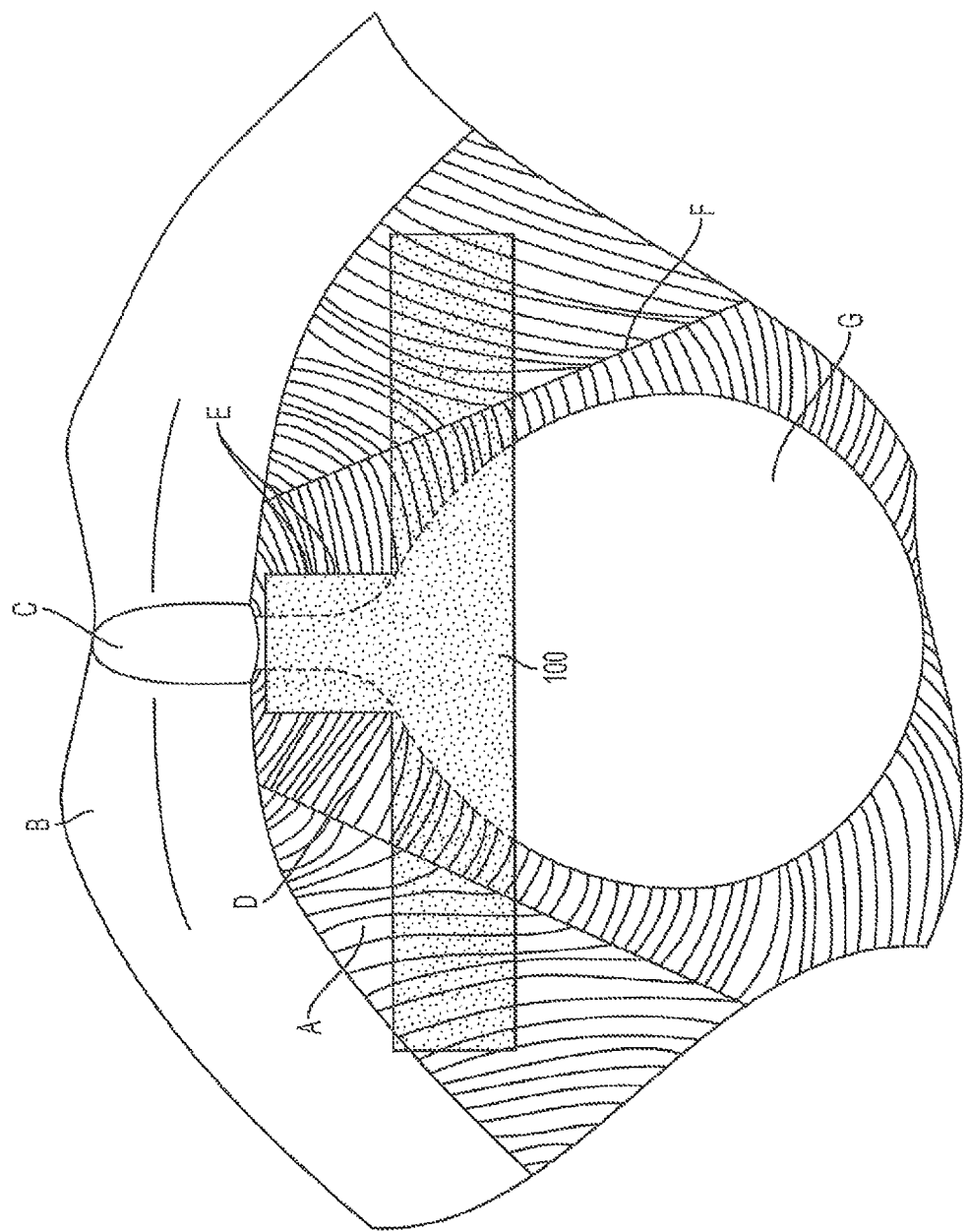
FIG. 1: Illustration of an embodiment of the implant (shown in silhouette) placed against the anterior surface of the bladder neck of an adult human female as seen through an anterior incision through the lower abdomen. The patient's anatomy is labeled as follows: A is the obturator internus, B is the pubic bone, C is the pubic symphysis, D is the endopelvic fascia, E is the periurethral fascia, F is the arcus tendineus, and G is the bladder.
Figure 2:
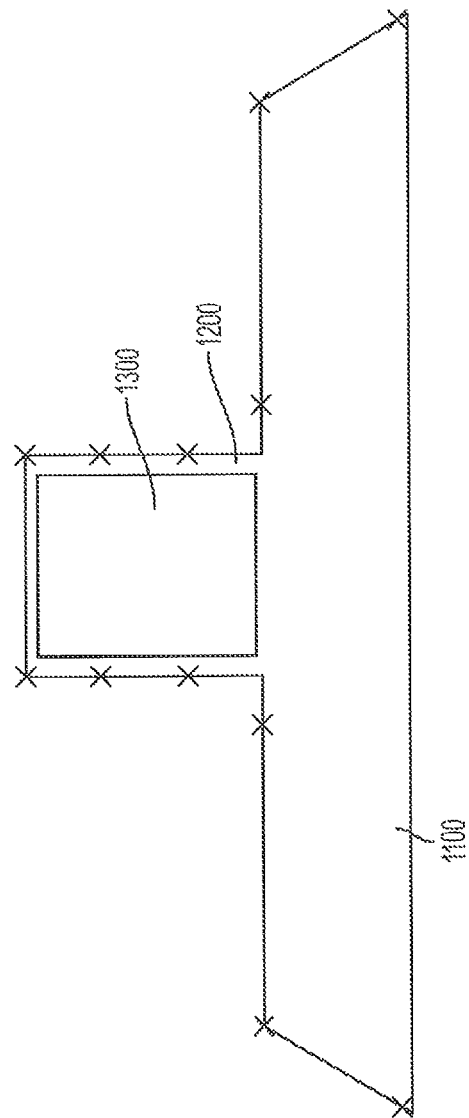
FIG. 2: Top view of an exemplary embodiment of the implant, with some potential anchor points marked as Xs.
Figure 3:
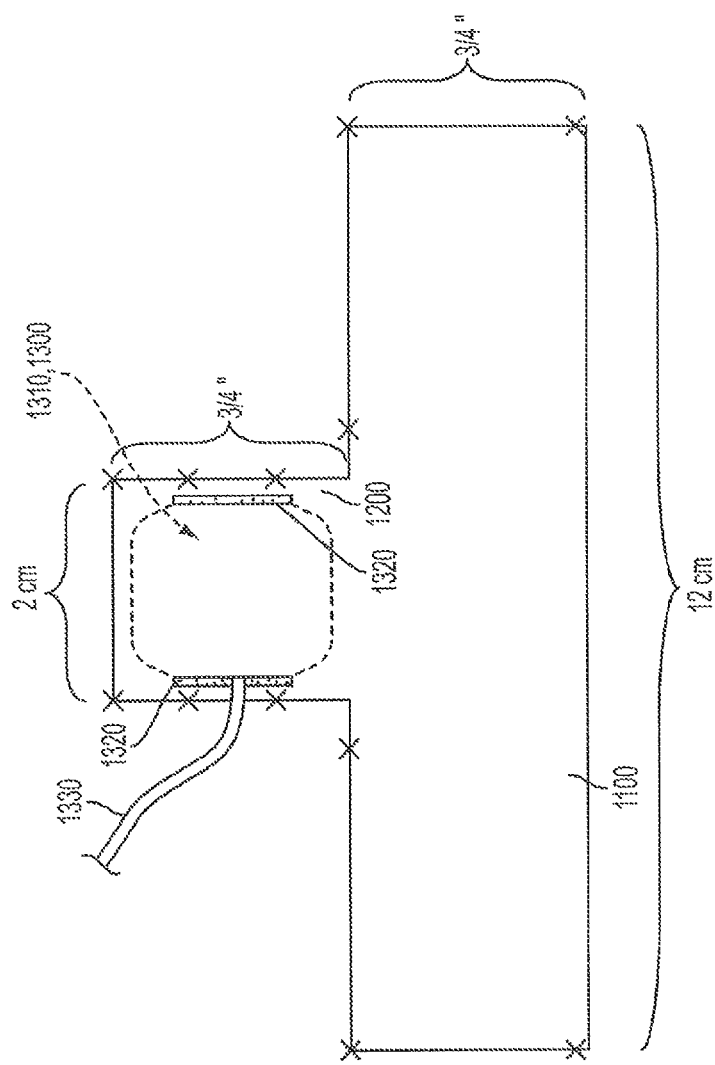
FIG. 3: Top view of another exemplary embodiment of the implant. Potential anchor points for suture fixation to structures such as the periurethral fascia, the pelvic fascia, and the anterior bladder shown as Xs.
Figure 4:
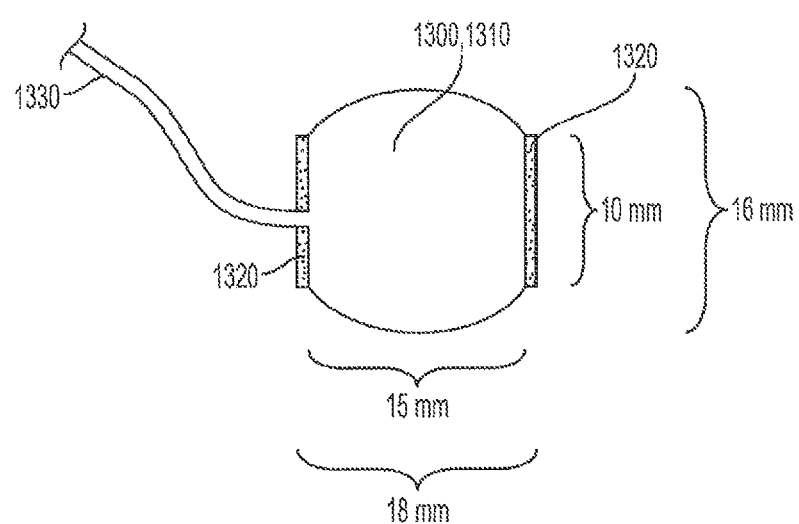
FIG. 4: Detail view of the expandable body of an exemplary embodiment of the implant.
Figure 5:
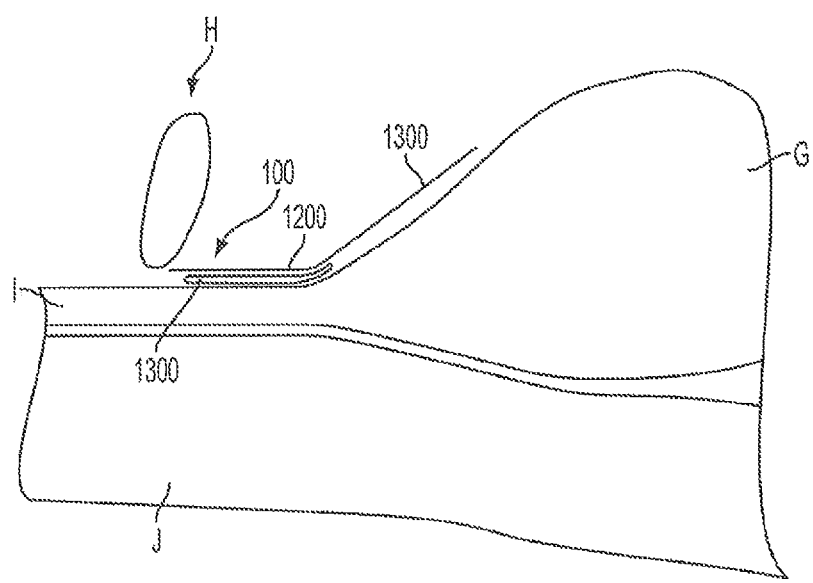
FIG. 5: Side view (sagittal cutaway) of an exemplary placement of an embodiment of the implant on the urethra when the expandable member is in its non-expanded configuration. The patient's anatomy is labeled as follows: G is the bladder, H is the pubic bone, I is the urethra, and J is the vagina.
Figure 6:
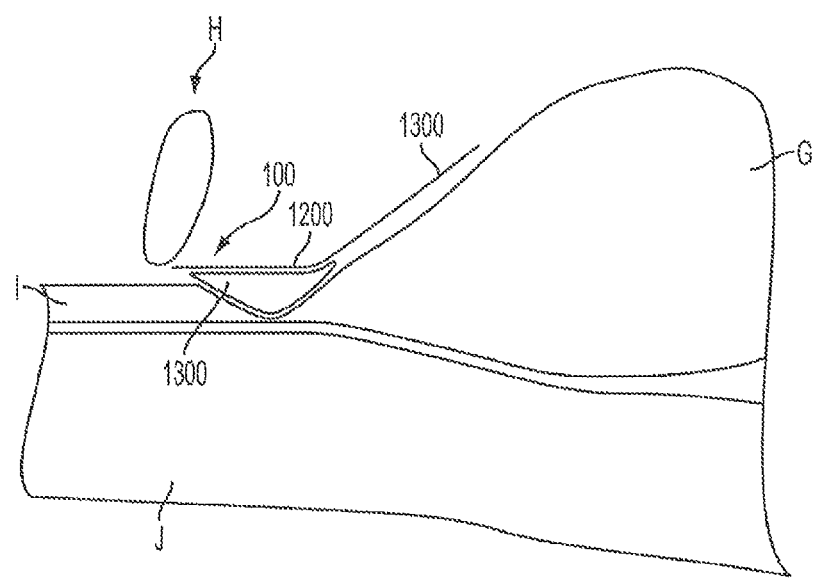
FIG. 6: Side view (sagittal cutaway) of the exemplary placement of the embodiment of the implant shown in FIG. 5 when the expandable member is in its expanded configuration. The patient's anatomy is labeled using the same reference characters as in FIG. 5.
Figure 7:
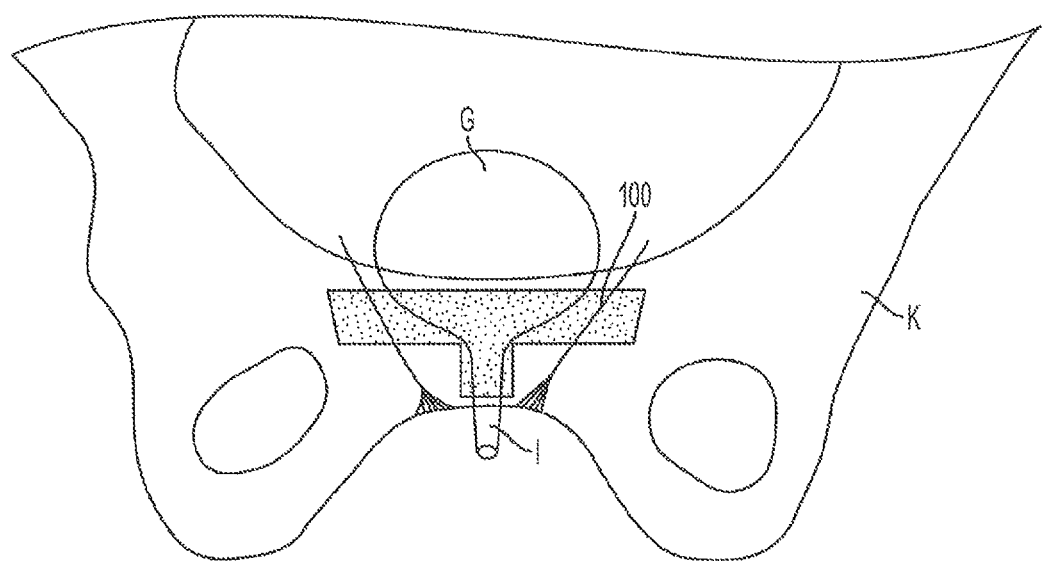
FIG. 7: Front view of an exemplary placement of an embodiment of the implant overlying the proximal urethra, bladder neck, and portion of the bladder. The patient's anatomy is labeled as follows: G is the bladder, I is the urethra, and K is the bony pelvis.
Figure 8:
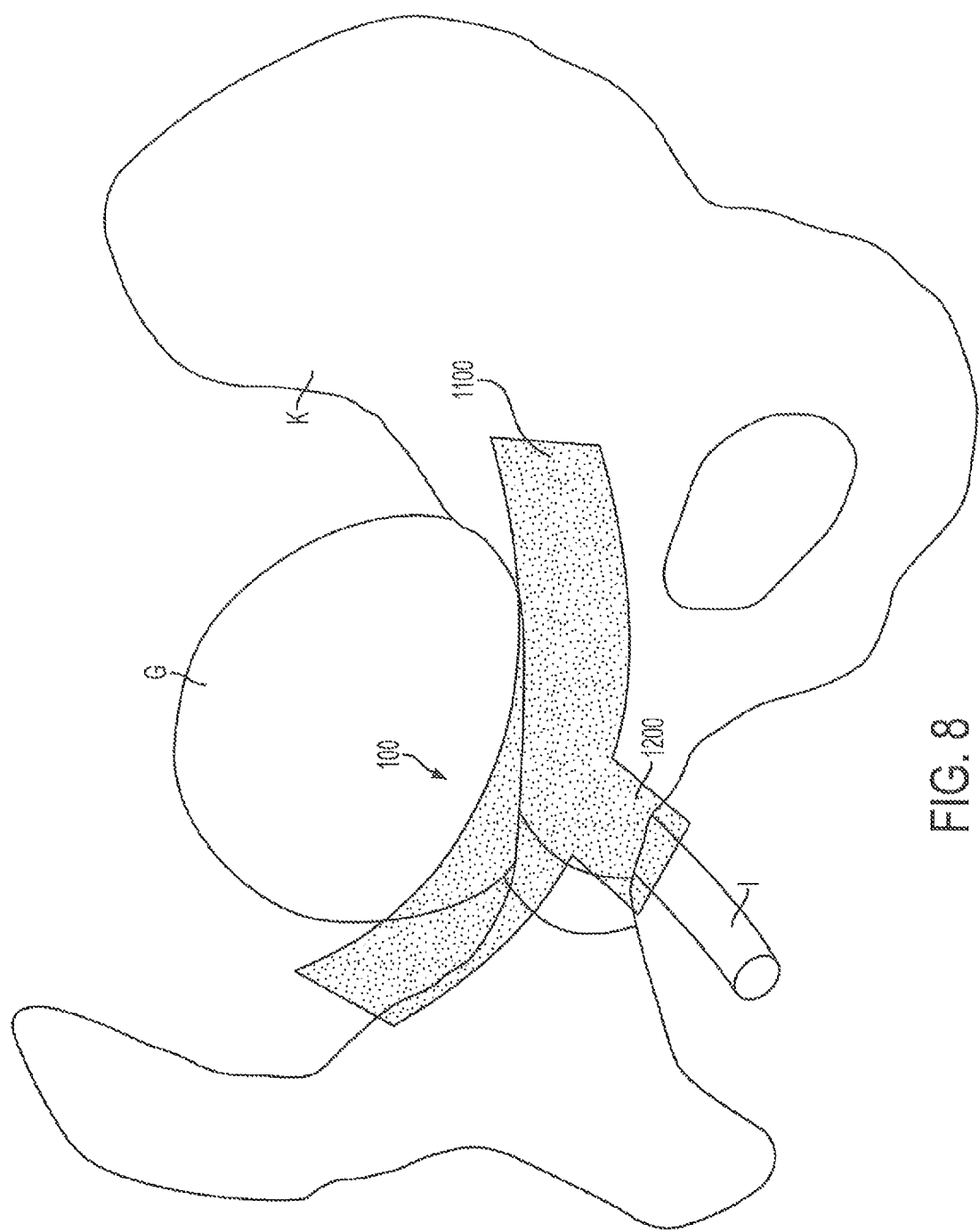
FIG. 8: Perspective view of the exemplary placement shown in FIG. 7. The patient's anatomy is labeled using the same reference characters as in FIG. 7.
Figure 9:
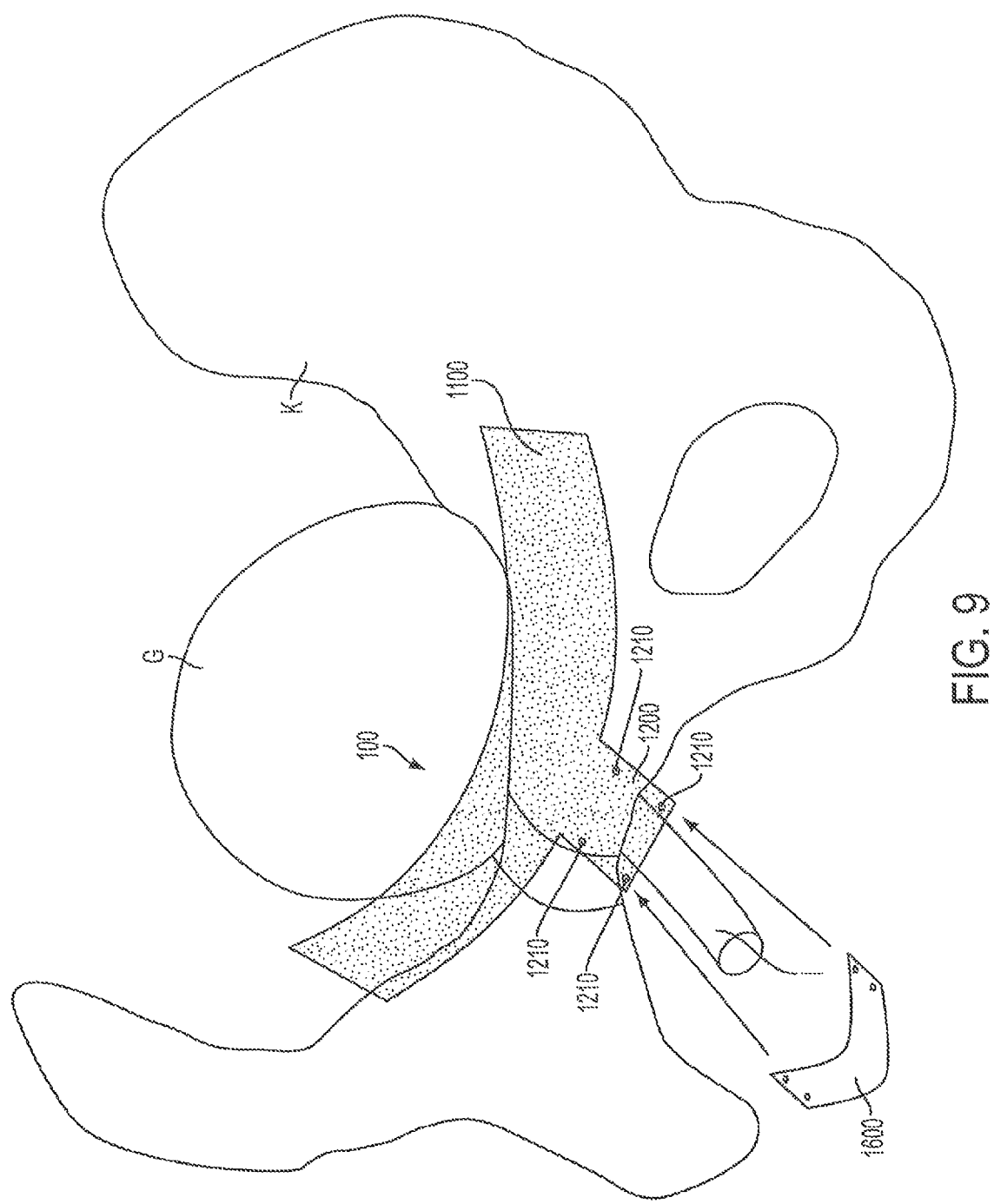
FIG. 9: Perspective view of an embodiment of the implant comprising a loop of suburethral graft. The patient's anatomy is labeled using the same reference characters as in FIG. 7.
Figure 10:
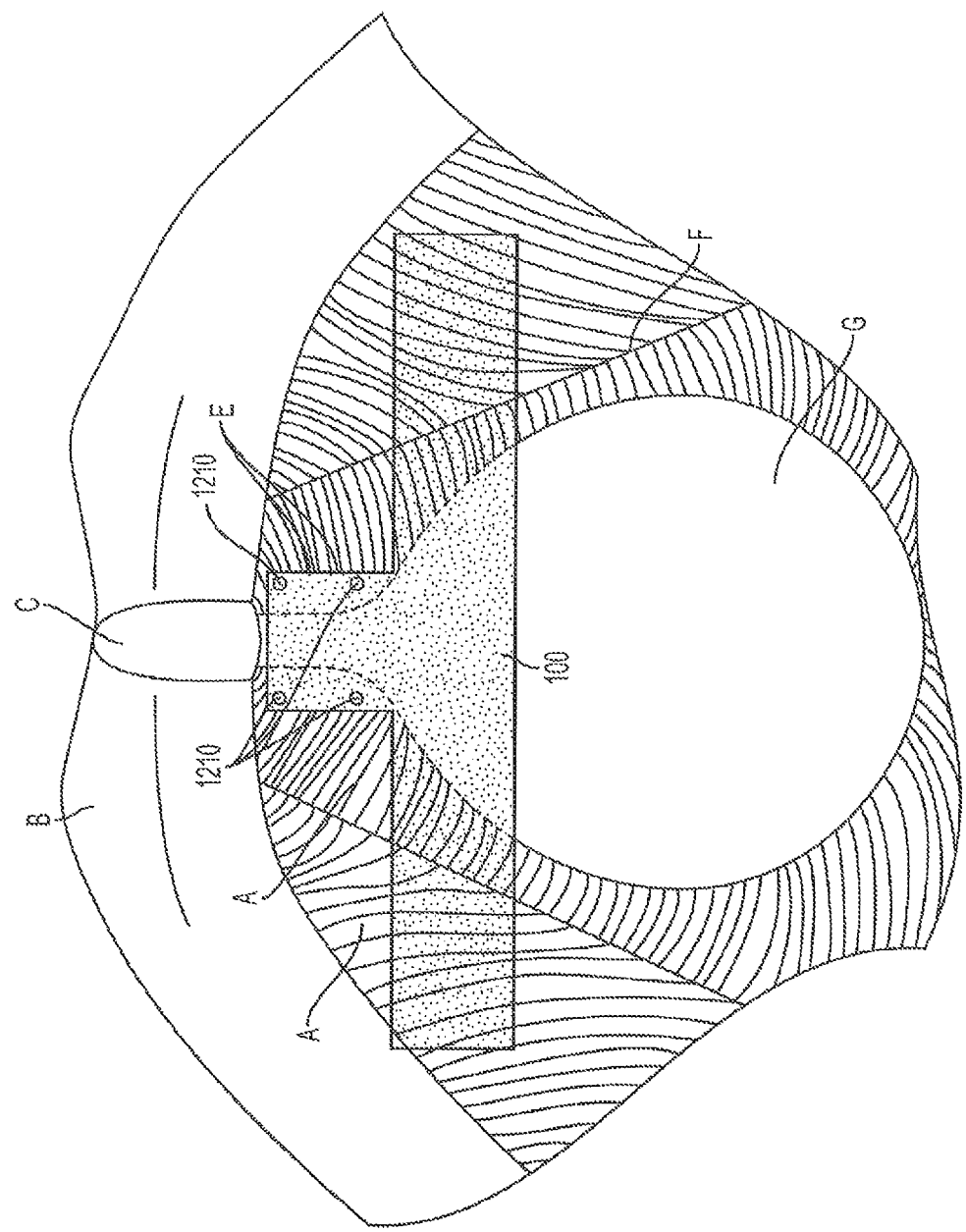
FIG. 10: Illustration of an embodiment of the implant (shown in silhouette) configured to be deployed with a loop of suburethral graft placed against the anterior surface of the bladder neck of an adult human female as seen through an anterior incision through the lower abdomen. The patient's anatomy is labeled using the same reference characters as in FIG. 1.

With reference to the use of the word(s) "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "consisting essentially of" means that, in addition to the recited elements, what is claimed may also contain other elements (steps, structures, ingredients, components, etc.) that do not adversely affect the operability of what is claimed for its intended purpose. Such addition of other elements that do not adversely affect the operability of what is claimed for its intended purpose would not constitute a material change in the basic and novel characteristics of what is claimed.

The terms "prevention", "prevent", "preventing", "suppression", "suppress" and "suppressing" as used herein refer to a course of action (such as implanting a medical device) initiated prior to the onset of a clinical manifestation of a disease state or condition so as to prevent or reduce such clinical manifestation of the disease state or condition. Such preventing and suppressing need not be absolute to be useful.

The terms "treatment", "treat" and "treating" as used herein refers to a course of action (such as implanting a medical device) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or device of the present disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or device of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than fold of a given value. Numerical quantities given herein are approximate unless stated otherwise, meaning that the term "about" or "approximately" can be inferred when not expressly stated.

B. Surgical Implant

A surgical implant 100 is provided with a relatively wide proximal portion 1100 and a relatively narrow distal portion 1200. The implant 100 can be used to maintain the position of a subject's urethra, compress the subject's urethra (for example to treat or prevent urinary incontinence), or both. The implant 100 is also useful to maintain the position of one or both of the bladder or the bladder neck. The implant 100 may be used to position or compress any portion of the urethra, but in particular embodiments the implant 100 is used to position or compress the proximal urethra. Any description herein that refers to the urethra generally may be construed to pertain to the proximal urethra specifically (although not to the exclusion of referring to the urethra generally). The implant 100 is configured to be anchored to the subject's pelvic fascia by the proximal portion 1100, so that the distal portion 1200 overlays and contacts the anterior surface of the urethra, as seen in the exemplary embodiment illustrated in FIG. 1.

In a general embodiment, the implant 100 comprises: a proximal portion 1100 having a width, length, and thickness, the width of the proximal portion 1100 being at least 4× its length and at least one hundred times (100×) its thickness, the proximal portion 1100 comprising a first non-absorbable biocompatible material; and a distal portion 1200 having a width, length, and thickness, the width of the distal portion 1200 being no more than one quarter (0.25×) the width of the proximal portion 1100, and the thickness of the distal portion 1200 being no more than one hundredth (0.01×) the width of the proximal portion 1100, the distal portion 1200 comprising a second non-absorbable biocompatible material.

In another general embodiment, the implant 100 comprises: a proximal portion 1100 having a first width, a first length, and a first thickness, comprising a first non-absorbable bio compatible material; and a distal portion 1200 having a second width, a second length, and a second thickness comprising the second non-absorbable biocompatible material; wherein the ratio of the first width to the second width is at least the ratio of the distance between a given human's right and left pectineal ligament to the distance between the given human's right and left periurethral fascia.

Given such dimensions, the implant 100 should be suitable for use on most female subjects, regardless of the absolute (as opposed to relative) size of the subject.

In some embodiments of the implant 100 one or both of the proximal or distal portions 1100 and 1200 are substantially non-elastic. In this context "non-elastic" refers to a relatively high Young's modulus, i.e., the proximal or distal portion 1100 & 1200 will not deform along an axis when opposing forces are applied along the axis. In this context polypropylene is considered to have a high Young's modulus (1.5-2.0 GPa), compared to rubber (0.01-0.1 GPa) and PTFE (0.5 GPa). Thus, in such embodiments the proximal and/or distal portion 1100 and 1200 will not tend to stretch when pulled in two opposite directions. A substantially non-elastic portion has the advantages of providing stronger support for the urethra and providing a rigid backing for the expandable member 1300 described below.

This is separate and distinct from the portion's flexibility. In some embodiments of the implant 100 one or both of the proximal or distal portions 1100 and 1200 will be flexible, regardless of whether said portion of the implant 100 is non-elastic. Although elasticity and flexibility sometimes go hand-in-hand, this is not the case for many types of materials. Everyday examples of materials with high flexibility but low elasticity are cotton textile fabrics; due to their fibrous construction they readily bend and fold, but if pulled in two opposite directions they do not stretch. Flexible portions have the advantage of being much easier to implant due to their ability to readily conform to the contours of the subject's body.

Accordingly, some embodiments of the first and second non-absorbable biocompatible material are flexible; some embodiments are substantially non-elastic; further embodiments are flexible and substantially non-elastic.

Suitable materials for such implants are known in the art. The implant 100 must be constructed from a non-absorbent biocompatible material. For example, one or both of the first and second non-absorbable biocompatible materials may be silicone (including stamped silicone), polymer fabric, or surgical mesh. One suitable type of polymer fabric is GORE-TEX (expanded polytetrafluoroethylene fabric). Various types of surgical mesh may be used, such as Type I macroporous mesh (pore size >75 μm), Type II microporous mesh (pore size <10 μm), and Type III macroporous mesh with multifilamentous filaments (pore size >75 μm). The materials for such meshes are known in the art. Examples include polypropylene, polyethylene, polytetrafluoroethylene, polyester (such as MERSILENE), SURGIPRO (polypropylene), PROLENE (polypropylene), or MARLEX (crystalline polypropylene and high-density polyethylene). In a specific embodiment the non-absorbent biocompatible material is Type I macroporous polypropylene mesh. The proximal and distal portions 1100 and 1200 may be constructed from different non-absorbent biocompatible materials, or they may be made from the same material. Using the same material has the advantage of ease of construction. Using different materials allows tailoring of the properties of each portion.

The dimensions of the implant 100 are suitable to anchor the proximal portion 1100 of the implant 100 to the pelvic fascia, to anchor the distal portion 1200 of the implant 100 to the periurethral fascia, and to contact the anterior surface of the urethra. Of course individual subjects vary in size, and to a lesser extent the relative dimensions of individual subjects vary as well. Nonetheless, one of ordinary skill in the art will have an understanding of the typical dimensions of a subject (including adult subjects, pediatric subjects, etc.) as well as an understanding of the upper and lower bounds of human variation in the relevant dimensions. The structure(s) in question may be a typical adult structure(s). Alternatively, the structure(s) in question may be wider or narrower than usual, but within the normal range for a human adult. In other embodiments of the implant 100 the structure(s) in question may deviate from the range of adult norms; for example in the case of a pediatric subject, a subject displaying dwarfism, and a subject displaying gigantism.

The proximal and distal portions 1100 and 1200 may be sufficiently thin to allow them to be implanted without altering the anatomical orientation of the subject's anatomy. In a specific embodiment of the implant 100 the thickness of one or both of the proximal portion 1100 and the distal portion 1200 is no more than about 1 mm. A thickness of 1 mm should be a suitable thickness for most subjects.

The distal portion 1200 is intended to cover a section of the subject's urethra (and optionally a portion of the bladder neck as well). Accordingly, some embodiments of the distal portion 1200 of the implant 100 have a width greater than the width of an adult human urethra.

The distal portion 1200 is also intended to be anchored to the subject's periurethral fascia. In some embodiments of the implant 100 the width of the distal portion 1200 is at least as great as the distance between a human's left and right periurethral fascia. Such embodiments of the distal portion 1200 can then be anchored to the left and right periurethral fascia of the subject when implanted. Excess material on the distal portion 1200 may be trimmed if not necessary for anchoring or covering the urethra. For typical human subjects, suitable widths of the distal portion 1200 may be, for example, at least about 14 mm, at least about 18 mm, and at least about 20 mm.

The proximal portion 1100 is intended to be anchored to pelvic structures. Accordingly, some embodiments of the proximal portion 1100 have a width greater than about the minimum distance between the right pelvic fascia and the left pelvic fascia of an adult human female. There is no upper bound to the width of the proximal portion 1100, as the proximal portion 1100 may be trimmed after manufacture to fit the individual subject. The proximal portion 1100 may in some cases be anchored to structures outside of the pelvic fascia, such as the pelvic periosteum. Some anchoring means may allow the proximal portion 1100 to be very slightly narrower than minimum distance between the right pelvic fascia and the left pelvic fascia, for example if the anchoring means cover the intervening distance between the pelvic fascia and the implant 100.

Some embodiments of the proximal portion 1100 are dimensioned to allow specific structures that are parts of the pelvic fascia to be used as anchor points. For example, in some embodiments of the implant 100 the width of the proximal portion 1100 is greater than about the minimum distance between the right pectineal ligament and the left pectineal ligament of the subject. In another example, the width of the proximal portion 1100 is greater than about the minimum distance between the right obturator fascia and the left obturator fascia of the subject. In yet another example, the width of the proximal portion 1100 is greater than about the minimum distance between the right obturator fascia and the left obturator fascia of an adult human female and less than the maximum distance between the right ilium and the left ilium of an adult human female.

The width of the proximal portion 1100 may also be defined in accordance with the absolute (as opposed to relative) dimensions of a typical adult human female. In some embodiments of the implant 100 the width of the proximal portion 1100 is at least about 7 cm or at least about 9 cm.

The implant 100 may further comprise an expandable member 1300 configured to apply pressure to the urethra when the implant 100 is in place. The expandable member 1300 is fastened to the distal portion 1200, and has a width adequate to achieve compression of the urethra that partially or wholly arrests the flow of urine. The expandable member 1300 has an expanded state and an unexpanded state. In some embodiments of the expandable member 1300, the expandable member 1300 is configured to primarily expand in a single direction. In some embodiments of the expandable member 1300 the expanded state protrudes in the posterior direction toward the urethra when in place in the subject. The expanded state may occupy a greater volume than the unexpanded state, but embodiments of the expandable member 1300 are contemplated in which the expanded state protrudes in the posterior direction toward the urethra when in place but does not increase in volume.

Some embodiments of the expandable member 1300 have a width greater than the width of a subject's urethra. This may relate to any subject as described above in the general discussion of the dimensions of bodily structures.

Some embodiments of the expandable member 1300 are inflatable (an inflatable member). The inflatable member is inflated with a fluid. The fluid may be introduced or removed through a conduit. In some embodiments of the implant 100 the fluid is exchanged between the inflatable member and a reservoir. When the member is inflated (for example to arrest a flow of urine) at least a portion of the fluid is transferred from the reservoir to the inflatable member. When the member is deflated (for example to allow the subject to urinate) at least a portion of the fluid is transferred from the member to the reservoir. Any suitable fluid may be used as known in the art. Examples include water, saline solution, and air. Water and saline have the advantages of being inexpensive, biocompatible in case of a leak, and incompressible. Air has the advantage of not requiring a reservoir (although one may be used).

Other versions of the expandable member 1300 do not operate by inflation. Some embodiments of the expandable member 1300 comprise a shaped memory material that compresses the urethra upon recovery of its shape after deformation. Other embodiments of the expandable member 1300 comprise a magnetic solenoid. Additional means for compressing the urethra are known in the art.

The dimensions of the expandable member 1300 will provide the desired compression of the urethra when expanded and still be sufficiently thin to be implanted when unexpanded. For example, in some embodiments of the implant 100 the thickness of the expandable member 1300 is no more than about 2 mm in the unexpanded state, and is about 8-10 mm in the expanded state. The expandable member 1300 may be substantially planar when unexpanded so as to fit in against the urethra without exerting pressure in the unexpanded state.

In embodiments of the expandable member 1300 that are inflatable, the expandable member 1300 may comprise a hollow balloon portion 1310. In further embodiments, the expandable member 1300 comprises a hollow balloon portion 1310 and a resilient anchor portion 1320 at the periphery of the balloon portion 1310. The anchor portion 1320 has sufficient tensile strength to be connected to the distal portion 1200 (such as by adhesives or fasteners) without failing.

Some embodiments of the expandable member 1300 are configured to primarily expand in the posterior direction. The expandable member 1300 will be constructed of a material that allows it to protrude in the posterior direction into the urethra in its expanded state. Some embodiments of the expandable member 1300 are constructed of material that is flexible, elastic, or both. In a specific embodiment of the implant 100 the expandable member 1300 is constructed of a flexible or elastic material, and the distal member is constructed of non-elastic material. This allows the distal member to act as a rigid backing for the expandable member 1300 when anchored in place, such that the expandable member 1300 will expand toward the urethra without pushing the distal portion 1200 outward in the anterior direction at the same time. Accordingly in some embodiments of the implant 100 the expandable member 1300 is confined by the distal portion 1200 against expansion in the anterior direction, distal direction, or proximal direction.

The expandable member 1300 need not surround or encircle the urethra in order to function properly. Some embodiments of the expandable member 1300 contact the urethra only on the anterior surface. Other embodiments of the expandable member 1300 contact the urethra over less than its entire circumference. Further embodiments of the expandable member 1300 contact the urethra over less than 180° of its circumference.

Alternatively, pressure may be exerted on the urethra by a bulge on the distal portion with a width greater than the width of an adult human urethra. The dimensions of the bulge may be any that are disclosed above as suitable for the expandable member. The bulge generally does not change in thickness (unlike the expandable member), but has a generally fixed thickness that does not completely arrest the flow of urine at all times. The bulge is dimensioned to compress the urethra to an extent to allow a patient with weakened pelvic floor muscles to control the flow, of urine, whereas without the additional compression provided by the bulge this would not be possible. The bulge may be any embodiment of the expandable member above, given that in such an embodiment the expandable member is expanded or inflated a certain amount, but thereafter remains of static thickness in the patient.

Some embodiments of the implant 100 comprise a loop of transvaginal graft 1600 fastened to the distal portion 1200 of the implant 100. The loop of transvaginal graft can function to provide opposing resistance on the posterior surface of the urethra for those patients in need of such additional opposing resistance. The graft can be made from any suitable graft material known in the art. Some embodiments of the graft material are made from autologous graft material, allograft material, and xenograft material. Specific examples of autologous graft material include material from the rectus fascia, the dermis, and the fascia lata. The loop of transvaginal graft 1600 will be dimensioned to be capable of encircling the urethra, and therefore will have a length at least equal to the circumference of a patient's urethra. In a specific embodiment the loop of transvaginal graft 1600 is approximately 2 cm wide by approximately 1.5-2.0 cm long. In embodiments of the implant 100 comprising the loop of transvaginal graft 1600, the distal portion 1200 may comprise one or more loop anchors 1210, for example grommets.

C. Methods

Method are provided related to the purposes of the implant 100 above, such as treating or preventing urinary incontinence, supporting the proximal urethra, supporting the bladder neck, and emplacing a surgical implant against the anterior urethra of a subject.

A general embodiment of the method comprises anchoring any of the implants 100 described above to a proximal structure and the periurethral fascia of a subject such that the distal portion 1200 contacts the anterior surface of the urethra. In some embodiments of the method the expandable member contacts the urethra of the subject.

Another general embodiment of the method is a method of emplacing a surgical implant against the anterior urethra of a subject, the method comprising: anchoring the proximal portion of an implant to a proximal structure of the subject so that the implant is positioned between the bladder and the pubic bone and in contact with the anterior surface of the bladder; and anchoring the distal portion of the implant to the right and left periurethral fascia of the subject; so that the distal portion of the implant contacts the anterior surface of at least one structure selected from: the bladder neck and the proximal urethra.

A further general embodiment of the method is a method of supporting the proximal urethra or bladder neck of a subject, comprising fixating one or both of the proximal urethra and the bladder neck from the anterior side. Specific embodiments may comprise fixating the proximal urethra from the anterior side. This general embodiment may further comprise contacting the proximal urethra or bladder neck from the anterior side with a substantially rigid implant anchored to a proximal structure.

Any of the above methods may comprise reversibly compressing the one or both of the proximal urethra and bladder neck from the anterior side to treat incontinence. Such compression may be achieved for example by contacting at least one of the proximal urethra and bladder neck with any expandable member as described above and expanding the expandable member.

The proximal structure to which the implant is anchored may be any that is described as suitable above. In certain embodiments the proximal structure may be selected from the group consisting of: the pelvic fascia, the obturator fascia, and the pectineal ligament. Some embodiments of the method comprise anchoring the distal portion to the public periosteum of the subject. This provides additional stability to the implant by anchoring its distal edge. Of course the implant must be dimensioned accordingly to allow the distal portion to be sufficiently close to the pubic periosteum for anchorage.

Anchoring may be achieved using any suitable anchoring means, such as soluble sutures, staples, and adhesives.

The method may comprise positioning the expandable member on the anterior surface of at least one of the proximal urethra and bladder neck. Thus positioned, the expandable member may be expanded to compress the proximal urethra and bladder neck to control incontinence.

Embodiments of any of the above methods may comprise inserting the implant through an incision in the lower abdomen of the subject.

The method may be performed openly or laparoscopically. One advantage of some embodiments of the anterior approach to emplacing the implant is that it may be performed robotically (as a form of laparos copy). The alternative transvaginal approach is too complex to be automated using current robotic technology. The advantages of robotic surgery are numerous, including permitting the procedure to be performed telesurgically, reducing the risk of infection, and allowing the use of microsurgical techniques.

D. Prophetic Example

In a non-limiting prophetic example, an implant 100 constructed of Type I macroporous polypropylene mesh will be implanted into a subject to treat urinary incontinence. The implant 100 will comprise: a proximal portion 1100 at least 10 cm wide, about 1 mm thick, and about 25 mm long; a distal portion 1200 about 18 mm wide, about 25 mm long, and about 1 mm thick; and an expandable member 1300 fastened to the distal portion 1200 that is configured to apply pressure on only the anterior surface of the urethra when in place.

After appropriate general anesthesia, the patient will be placed in a low lithotomy position. A lower abdominal prep will be carried out as well as a full vaginal prep. A Foley catheter will be placed in the bladder.

A Pfannenstiel-style incision will be made and tissue will be dissected down to the level of the rectus fascia. Dissection will be carried out through the rectus fascia and into the space of Retzius. Stationary retractors will be used for exposure.

The fibrofatty tissue will be bluntly dissected off the undersurface of the pubic bone. This will provide exposure to the bladder, urethra, and the pelvic fascia.

Two fingers will be placed in the vaginal area in order to lift up on the anterior vaginal wall. The other hand will retract on the bladder neck with the balloon of the Foley as a guide. The proximal urethra and bladder neck will be exposed.

Blunt dissection will be carried out to the pelvic sidewall in order to well visualize the endopelvic fascia as well as the arcus tendineus and other fascia structures of the pelvis.

The aforementioned non-absorbable implant 100 with expandable body will be placed into the pelvis. This will be positioned with the distal segment of the implant 100 overlaying the proximal urethra. Some of the distal segment may overlay a portion of the bladder neck. The proximal segment of the implant 100 will be positioned over the anterior bladder and bladder neck area. The more lateral portions of the proximal segment will be laid over the pelvic sidewall fascia. Excess mesh from the lateral portions will be excised if longer than the width of the pelvic fascia. The non-absorbable material at any location will be trimmed (excluding the expandable body area) if necessary to custom fit to the patient's pelvic anatomy.

Interrupted Vicryl sutures will be used to fixate the mesh at different locations in the pelvis. The more distal segment will be fixated to the periurethral fascia as it enters under the pubic bone. More fixation sutures will be placed on the lateral borders of the distal segment as the fascia continues to the bladder neck area.

Lateral fixation of the proximal segment will be carried out with interrupted sutures. Fixation points include the endopelvic fascia, arcus tendineus and in some situations depending on the patient's anatomy, the obturator internus or the pectineal ligament.

The sutures will be placed on the more proximal segment to allow it to lay flat on the endopelvic fascia as it approaches the arcus tendineus. The implant 100 will not be placed under tension.

After the implant 100 appears to be in good position, the tubing 1330 from the expandable body will be connected to a syringe and inflated. This will allow visualization to verify that it stays in place while the expandable body provides compression on the proximal urethra in a posterior direction.

Cystourethroscopy will be carried out to visualize complete closure of the proximal urethra. After this confirmation, the expandable body will be deflated.

A reservoir with fluid will be placed into the left lower pelvis. A trocar will be placed posterior to the left side of the pubic bone and punctured out through the left genital area just lateral to the left labia. This will be affixed to another more blunt trocar with a hook that will be pulled into the pelvis. This trocar with a hook is attached to the ends of the tubing 1330 from the expandable body and the reservoir. Both tubings will be pulled out of the pelvis lateral to the left labia.

The abdomen will be irrigated and the rectus fascia and skin will be closed.

Attention will be placed on the paravaginal area at the location of the tubing 1330 and the puncture site. An incision will be carried out at that location superiorly and inferiorly. A pocket will be created within the labia in order to place the pump. Excess tubing will be cut from the reservoir and the expandable body and attached to the pump.

The pump will be placed in this pouch, the area will be copiously irrigated, and the skin will be closed. The Foley catheter can be removed and the expandable body shall remain in the non-inflated position during the perioperative period.

E. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

I claim:

1. A method of supporting at least one of the proximal urethra or bladder neck of a female subject, the method comprising: supporting the at least one of the proximal urethra or bladder neck with a non-elastic implant only from the anterior side by fixating the implant to a proximal structure of the subject so that the implant is positioned between the bladder and the pubic bone and in contact with the bladder only at its anterior surface; and fixating the implant to the right and left periurethral fascia of the subject; wherein said implant comprises a non-absorbent biocompatible material.

2. The method of claim 1, comprising: inserting the implant through an incision in the lower abdomen of the subject.

3. The method of claim 2, wherein said incision in the lower abdomen is at least one of an open incision or a laparoscopic incision.

4. The method of claim 1, wherein the implant is not inserted via a transvaginal approach.

5. The method of claim 1, comprising: reversibly compressing at least one of the proximal urethra or bladder neck from only the anterior side to treat incontinence.

6. The method of claim 1, comprising: wherein the proximal structure is selected from the pelvic fascia, obturator fascia, arcus tendineous, and the pectineal ligament.

7. The method of claim 6, comprising anchoring the implant to the pubic periosteum.

8. The method of claim 1, wherein the patient suffers from urinary incontinence.

9. The method of claim 1, comprising prior to fixating the implant:
   making a Pfannenstiel incision in the subject;
   dissecting the subject's tissue down to the level of the rectus fascia; and
   dissecting through the rectus fascia and into the space of Retzius.

10. The method of claim 9, comprising: bluntly dissecting fibrofatty tissue off the undersurface of the pubic bone; and exposing the bladder, urethra, and pelvic fascia.

11. The method of claim 10, comprising:
   lifting the anterior vaginal wall;
   retracting the bladder neck; and
   exposing the proximal urethra and bladder neck.

12. The method of claim 11, comprising performing blunt dissection out to the pelvic sidewall sufficiently to visualize one or both of the endopelvic fascia and the arcus tendineus.

13. The method of claim 1, comprising prior to fixating the implant:
   making a laparoscopic incision in the subject;
   dissecting the subject's tissue down to the level of the rectus fascia; and
   dissecting through the rectus fascia and into the space of Retzius.

14. The method of claim 1, wherein the implant comprises an expandable member positioned to exert pressure on the urethra from only the anterior side.

15. The method of claim 14, wherein the expandable member is configured to primarily expand in a direction toward the urethra.

16. The method of claim 14, comprising fastening a loop to the implant, said loop positioned to oppose, from the posterior side, pressure exerted by the expandable member on the urethra.

17. The method of claim 16, wherein the loop is the only portion of the implant in contact with the urethra from the posterior side.

18. The method of claim 1, wherein the implant is flexible.

19. The method of claim 1, wherein the implant is constructed from macroporous mesh.

20. The method of claim 1, wherein the implant comprises a distal portion and a proximal portion at least 5 times as wide as the distal portion.

21. The method of claim 1, wherein the bladder neck or urethra is provided support sufficient to correct urethral prolapse.

22. The method of claim 1, wherein support is imparted to the bladder neck or urethra is provided support sufficient to correct urethral hypermobility.

23. The method of claim 1, wherein support is imparted to the bladder neck or urethra is provided support sufficient to prevent or treat distal bladder prolapse.

24. The method of claim 1, wherein the non-elastic implant is configured to compress the anterior urethra.

* * * * *